United States Patent …

(12) United States Patent
Tran et al.

(10) Patent No.: US 6,884,259 B2
(45) Date of Patent: Apr. 26, 2005

(54) MULTI-LENGTH DELIVERY SYSTEM

(75) Inventors: Khanh Tran, Coon Rapids, MN (US); Steve M. Spencer, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/649,079

(22) Filed: Aug. 27, 2003

(65) Prior Publication Data

US 2004/0098083 A1 May 20, 2004

Related U.S. Application Data

(62) Division of application No. 09/681,462, filed on Apr. 11, 2001, now Pat. No. 6,660,031.

(51) Int. Cl.$^7$ ................................................. A61F 2/06
(52) U.S. Cl. .................................... 623/1.12; 606/108
(58) Field of Search .............................. 623/1.11, 1.12; 606/108

(56) References Cited

U.S. PATENT DOCUMENTS

| | | | |
|---|---|---|---|
| 4,955,889 A | 9/1990 | Van Gent | 606/107 |
| 5,308,316 A * | 5/1994 | Williams et al. | 604/13 |
| 5,534,007 A | 7/1996 | St. Germain et al. | 606/108 |
| 5,653,691 A | 8/1997 | Rupp et al. | 604/96 |
| 5,690,644 A | 11/1997 | Yurek et al. | 606/108 |
| 5,772,669 A | 6/1998 | Vrba | 606/108 |
| 5,776,141 A | 7/1998 | Klein et al. | 606/108 |
| 5,792,144 A | 8/1998 | Fischell et al. | 606/108 |
| 5,817,102 A | 10/1998 | Johnson et al. | 606/108 |
| 5,833,694 A | 11/1998 | Poncet | 606/108 |
| 5,868,755 A | 2/1999 | Kanner et al. | 606/108 |
| 5,911,452 A | 6/1999 | Yan | 29/516 |
| 5,944,726 A | 8/1999 | Blaeser et al. | 606/108 |
| 5,957,930 A | 9/1999 | Vrba | 606/108 |
| 5,980,533 A | 11/1999 | Holman | 606/108 |
| 5,989,280 A | 11/1999 | Euteneuer et al. | 606/198 |
| 6,018,857 A | 2/2000 | Duffy et al. | 29/407.01 |
| 6,042,588 A | 3/2000 | Munsinger et al. | 606/108 |
| 6,059,813 A | 5/2000 | Vrba et al. | 606/198 |
| 6,090,035 A | 7/2000 | Campbell et al. | 600/7 |
| 6,113,608 A | 9/2000 | Monroe et al. | 606/108 |
| 6,120,522 A | 9/2000 | Vrba et al. | 606/190 |
| 6,139,524 A | 10/2000 | Killion | 604/102 |
| 6,143,021 A | 11/2000 | Staehle | 623/1.11 |
| 6,156,062 A | 12/2000 | McGuinness | 623/1.11 |
| 6,168,617 B1 | 1/2001 | Blaeser et al. | 623/1.11 |
| 6,183,504 B1 | 2/2001 | Inoue | 623/1.11 |
| 6,190,360 B1 | 2/2001 | Iancea et al. | 604/164.09 |
| 6,228,051 B1 * | 5/2001 | Trumbull | 604/95.02 |
| 6,238,410 B1 | 5/2001 | Vrba et al. | 606/198 |
| 6,254,611 B1 | 7/2001 | Vrba | 606/108 |
| 6,383,211 B1 | 5/2002 | Staehle | 623/1.11 |
| 6,391,050 B1 | 5/2002 | Broome | 623/1.11 |
| 6,423,059 B1 * | 7/2002 | Hanson et al. | 606/41 |
| 6,506,201 B2 | 1/2003 | Di Caprio et al. | 606/192 |
| 6,514,261 B1 | 2/2003 | Randall et al. | 606/108 |
| 6,530,947 B1 | 3/2003 | Euteneuer et al. | 623/1.11 |
| 6,544,278 B1 | 4/2003 | Vrba et al. | 606/198 |
| 6,572,643 B1 | 6/2003 | Gharibadeh | 623/1.11 |

FOREIGN PATENT DOCUMENTS

| | | |
|---|---|---|
| DE | 25 04 663 A | 8/1976 |
| WO | 96/26689 | 9/1996 |
| WO | 00/30562 A1 | 6/2000 |
| WO | 09/681462 | 4/2001 |

* cited by examiner

*Primary Examiner*—Corrine McDermott
*Assistant Examiner*—Thomas J Sweet
(74) *Attorney, Agent, or Firm*—Vidas, Arrett & Steinkraus (57) ABSTRACT

A stent delivery system may comprise a shape memory metal bumper which is expandable from a reduced profile configuration to an increased profile configuration. The stent delivery system comprises an inner tube, a stent disposed about the inner tube and a shape memory metal bumper disposed about the inner tube adjacent the proximal end of the stent.

12 Claims, 8 Drawing Sheets

MULTI-LENGTH DELIVERY SYSTEM

This application is a divisional application of U.S. application Ser. No. 09/681,462, filed Apr. 11, 2001, now U.S. Pat. No. 6,660,031, which is herein incorporated by reference in its entirety.

BACKGROUND OF INVENTION

A stent may be loaded onto a catheter inner tube either from the distal end of the inner tube or from the proximal end of the inner tube. When the stent is loaded from the distal direction, however, the tip of the catheter may interfere with the stent. To avoid obstruction from the tip, the stent as loaded must have an opening wide enough to allow passage of the tip therethrough which causes issues in device performance. When the stent is loaded from the proximal direction, the stent may be obstructed by any proximal bumpers present on the inner tube. Typically, a bumper is provided proximal to the stent receiving region of the catheter inner tube to aid in delivering the stent from the catheter. To avoid obstruction from the bumper, the stent as loaded must have an opening wide enough to allow passage of the bumper therethrough, again causing issues with device performance.

Once the stent has been loaded on the catheter, a retractable sheath is typically placed over the stent. A number of devices for retracting a retractable sheath are known in the art. Patents disclosing retractable sheaths include U.S. Pat. No. 5,772,669 and U.S. Pat. No. 5,868,755. With many retraction systems, it is necessary to move a portion of the manifold by a distance at least equal to the length of the loaded stent to retract the sheath.

While a number of patents such as U.S. Pat. No. 6,090,035, U.S. Pat. No. 6,018,857 and U.S. Pat. No. 5,911,452 have dealt with the issue of stent loading, there remains a need for innovative methods of loading self-expanding stents onto catheters as well as for innovative catheters that facilitate this stent loading. There also remains a need for innovative catheters having retractable sheaths and sheath retraction mechanisms having a mechanical advantage to facilitate sheath retraction.

All U.S. patents, patent applications and other published documents mentioned anywhere in this application are incorporated herein by reference in their entirety.

Without limiting the scope of the invention, a brief summary of various embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF INVENTION

In one embodiment, the present invention is directed to a stent delivery system comprising an inner tube having a proximal end and a distal end, a stent receiving region and a stent disposed about the stent receiving region of the inner tube. The delivery system further comprises a shape memory metal bumper disposed about the inner tube at a position adjacent the proximal or distal end of the stent. Desirably, the stent receiving region is at the distal end of the inner tube and the shape memory bumper is adjacent the proximal end of the stent.

The present invention is also directed in another embodiment to a delivery system for delivering an implantable medical device to a bodily lumen. The delivery system comprises an inner tube having a proximal end, a distal end and a medical device receiving region. An implantable medical device is disposed about the medical device receiving region of the inner tube. A shape memory metal bumper is disposed about the inner tube at a position adjacent the proximal or distal end of the implantable medical device. Desirably, the medical device receiving region is adjacent to the distal end of the inner tube and the shape memory bumper is adjacent the proximal end of the implantable medical device.

The present invention is further directed to a device delivery system comprising an inner tube having a proximal end, a distal end and a medical device receiving region. Desirably, the medical device receiving region is adjacent to the distal end of the inner tube. An implantable medical device is disposed about the medical device receiving region of the inner tube. A shape memory metal bumper is disposed about the inner tube at a position adjacent to the distal end or more desirably, the proximal end of the implantable medical device. The shape memory metal bumper is transformable between a martensitic state and an austenitic state. In the martensitic state, the shape memory metal bumper has a reduced profile. In the austenitic state, the shape memory metal bumper has an increased profile.

The present invention is also directed to a method of preparing a stent delivery system. In accordance with the inventive method, a tube having a proximal end and a distal end is provided. The distal end of the tube terminates in an enlarged tip. The tube has a bumper formed of a shape memory metal proximal to the tip. The bumper is expandable from a reduced profile state to an increased profile state. The bumper is in the reduced profile state. A stent having a flow passage therethrough sized to allow passage of the bumper therethrough when the bumper is in the reduced profile state is provided. The stent is passed about the bumper and the stent disposed about the inner tube adjacent to the bumper, between the bumper and the tip. Finally, the bumper is caused to transition from the reduced profile state to the increased profile state.

In another embodiment, the invention is directed to a medical device delivery system comprising a manifold having a rack and pinion. An inner tube extends distally from the manifold. A retractable sheath is disposed about the distal end of the inner tube. A pull-wire extends proximally from the retractable sheath to the manifold. The pull wire is attached to the pinion. The sheath may be retracted by moving one of the rack and pinion relative to the other.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

Figure 1:
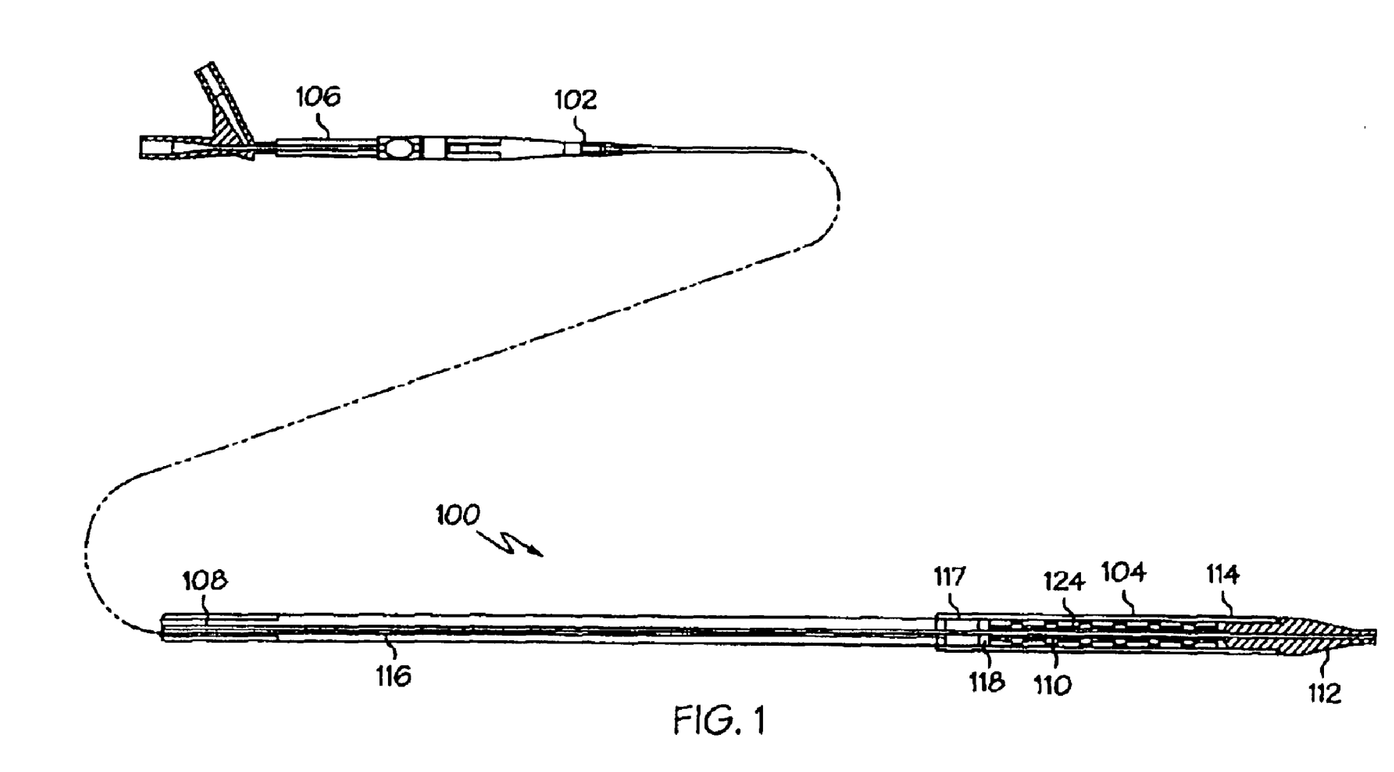
FIG. 1 shows a side view of a medical device delivery system according to the invention including a cross-sectional view of the distal portion thereof and a side view of the proximal end showing the manifold portion thereof.
Figure 2:
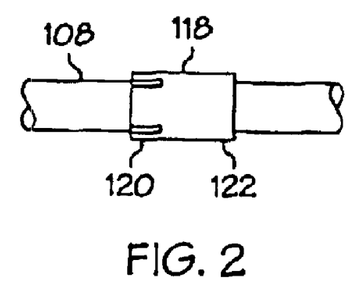
FIG. 2 shows a side elevational view of a bumper in a reduced profile configuration disposed about an inner tube according to the invention.
Figure 3:
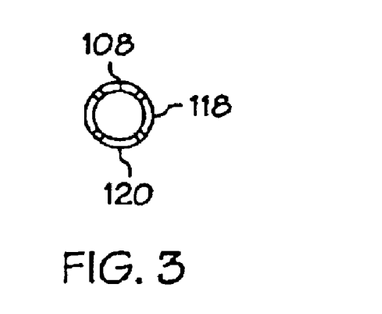
FIG. 3 is a cross-sectional view of the slotted portion of the bumper of FIG. 2.

A medical device delivery system is shown generally at 100 in FIG. 1. Medical device delivery system has a proximal end 102 and a distal end 104. Manifold 106 is provided at proximal end 102. Inner tube 108 extends distally from manifold 106. The inner tube includes a medical device receiving region 110, desirably towards the distal end of inner tube 108. Inner tube 108 terminates at the distal end in a tip 112. Tip 112 may be integrally formed with the inner tube or may be bonded to the inner tube using any suitable bonding technique including adhesive bonding, heat welding or laser bonding. A retractable sheath 114 is disposed about the distal end of inner tube 108. Pull wire 116 extends proximally from retractable sheath 114 to the region of manifold 106. Retractable sheath 114 may be retracted by pulling pull wire 116 in the proximal direction.

Figure 4:
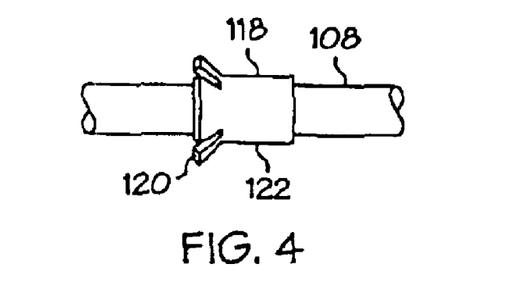
FIG. 4 shows a side elevational view of a bumper in a partially expanded configuration disposed about an inner tube according to the invention.
Figure 5:
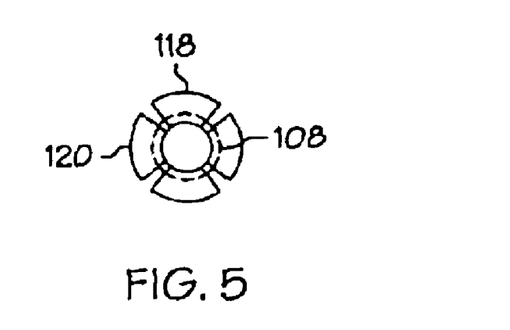
FIG. 5 is a cross-sectional view of the slotted portion of the bumper of FIG. 4.
Figure 6:
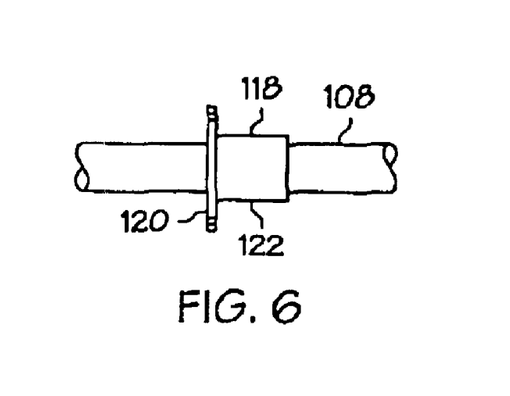
FIG. 6 shows a side elevational view of a bumper in an expanded profile configuration disposed about an inner tube according to the invention.
Figure 7:
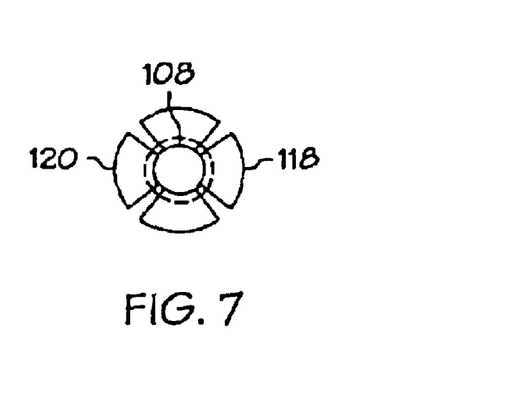
FIG. 7 is a cross-sectional view of the slotted portion of the bumper of FIG. 6.

Medical device delivery system 100 further comprises a shape memory metal bumper 118 disposed about the inner tube adjacent to medical device receiving region 110. Desirably, the shape memory bumper is adjacent the proximal end of the medical device receiving region. Shape memory metal bumper 118 may be affixed to inner tube 108 using any suitable adhesive or using any other suitable method for affixing a bumper to a tube. Shape memory metal bumper is transformable between a reduced profile configuration, as shown in greater detail in FIGS. 2–3 and an increased profile configuration, as shown in greater detail in FIGS. 4–7. In the embodiment of FIGS. 2–7, shape memory metal bumper 118 is in the form of a tube having a slotted portion 120 and a non-slotted portion 122. Shape memory metal bumper 118 is shown in FIGS. 4–5 as it transitions from the reduced profile configuration to the increased profile configuration. Slotted portion 120 of tube 118 is partially open. In FIGS. 6–7, slotted portion 120 of tube 118 is fully open. In the fully open configuration, the shape memory metal bumper may optionally extend radially outward from the inner tube to a distance in excess of the stent.

Any of the medical device delivery systems disclosed herein may also be provided with two shape memory metal bumpers with one of the shape memory metal bumpers proximal to the medical device or stent and the other shape memory metal bumper distal to the medical device or stent.

Shape memory metal bumpers having other shapes may also be used. For example, one or more arcuate shape memory metal bumpers which do not extend all the way around the inner tube may be used. More generally any shape memory metal bumper of any shape may be used as long as the bumper has a reduced profile configuration in which the bumper may be passed through the flow passage of a stent or other medical device and an increased profile configuration in which it cannot pass through the flow passage of a medical device such as a stent.

Shape memory metal bumper 118 may be made of any suitable, biocompatible shape memory metal. Examples of shape memory metals which may be used include nickel-titanium alloy, generically known as nitinol, copper-aluminum-nickel, copper-zinc-aluminum and iron-manganese-silicon alloys.

Desirably, the shape memory metal bumper will be made of Nitinol. Nitinol has two phase, a martensitic phase and an austenitic phase. A slotted tube of Nitinol may be formed to a desired shape such as that shown in FIGS. 6 and 7 and the shape heat set into position. The Nitinol may then be cooled while maintaining its shape and then plastically deformed to a new shape such as that shown in FIGS. 2 and 3. Upon subsequent heating, the metal will return to the shape it originally had prior to plastic deformation at the cold temperature.

Medical device delivery system 100 may be used to deliver a variety of implantable medical devices including stents and vena cava filters. It is noted that for the purposes of this disclosure, the term stent is understood to refer to stents, grafts, stent-grafts and other expandable prostheses. As shown in FIG. 1, stent 124 is disposed about medical device receiving region 110 of inner tube 108. Stent 124 is desirably a self-expanding stent. An example of a suitable stent for use with the medical device delivery system is a shape memory metal stent such as the Scimed Radius™ stent disclosed in WO 96/26689.

The inventive medical device delivery systems may also be modified for use with balloon expandable stents by providing an inflatable medical balloon in the medical device receiving region and an inflation lumen for supplying an inflation fluid to the balloon. An example of a medical device delivery system with a balloon is shown in commonly assigned U.S. Pat. No. 5,989,280.

The inventive medical device delivery systems described above may be provided in an over-the-wire configuration, a rapid exchange configuration or a fixed wire configuration. Examples of catheters with such configurations are disclosed in U.S. Pat. No. 5,980,533 and U.S. Pat. No. 5,957,930.

Figure 8A:
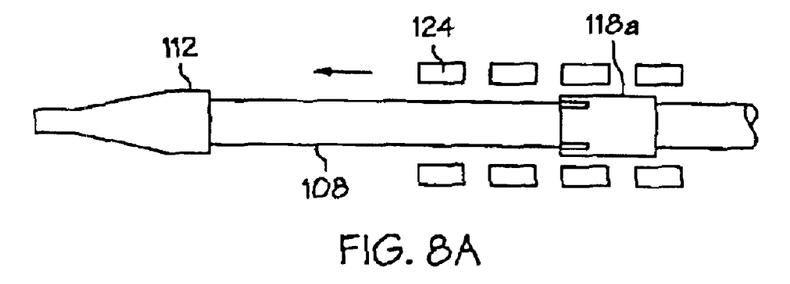
FIGS. 8a–c illustrate a process for loading a stent on a catheter according to the invention with the distal end of the catheter shown in longitudinal cross-section.
Figure 8B:
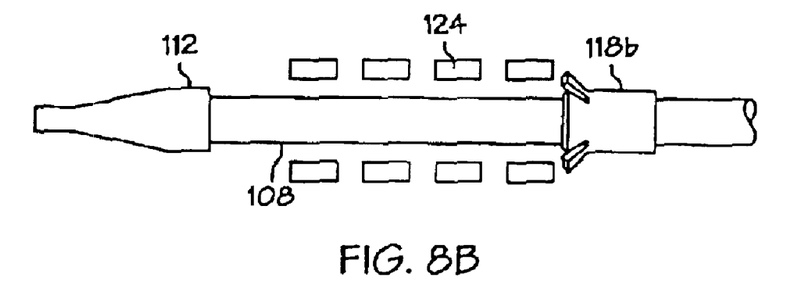
Figure 8C:
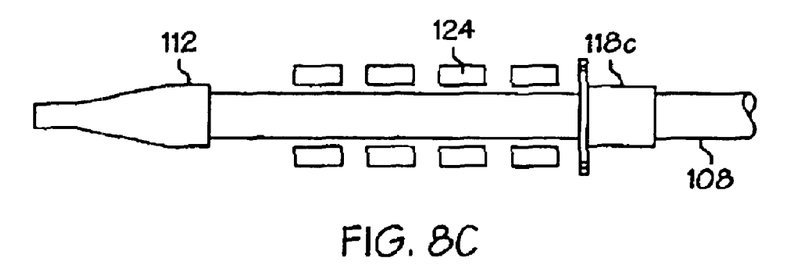

The present invention is also directed to a method of preparing a delivery system for delivering an implantable medical device. In accordance with the inventive method, as shown in FIG. 8a, a tube 108 having a proximal end and a distal end is provided. The distal end of tube 108 terminates in an enlarged tip 112. Tube 108 has a bumper 118 formed of a shape memory metal proximal to tip 118. Bumper 118 is expandable from a reduced profile state to an increased profile state. An implantable medical device having a flow passage therethrough sized to allow passage of the bumper in the reduced profile state therethrough, such as stent 124, is provided. As further shown in FIG. 8a, the implantable medical device is passed about the bumper in the reduced profile state 118a and the implantable medical device disposed about the inner tube adjacent to the bumper, between the bumper and the tip. Finally, the bumper is caused to transition from the reduced profile state to a partially increased profile state 118b as shown in FIG. 8b, and then to the fully increased profile state 118c as shown in FIG. 8c.

The transitioning of the bumper to the increased profile configuration may be caused by increasing the temperature of the bumper. Where the bumper is made of a shape memory metal having a martensitic state and an austenitic state with associated austenitic start and finish temperatures, the temperature of the bumper may be increased to a temperature exceeding the austenitic start temperature thereby causing the bumper to transition from the reduced profile state to the increased profile state. The specific type of Nitinol should be chosen such that the austenitic start or finish temperature is not so high that the tube would be damaged by heating the bumper.

The inventive method may optionally further comprise the step of providing a manifold to the proximal end of the inner tube subsequent to disposing the medical device adjacent to the bumper. Moreover, the method may optionally include the step of providing a retractable sheath about the implantable medical device prior to or subsequent to disposing the implantable medical device about the inner tube adjacent to the bumper.

The inventive method may be used in conjunction with a variety of implantable medical devices including stents.

Figure 9:
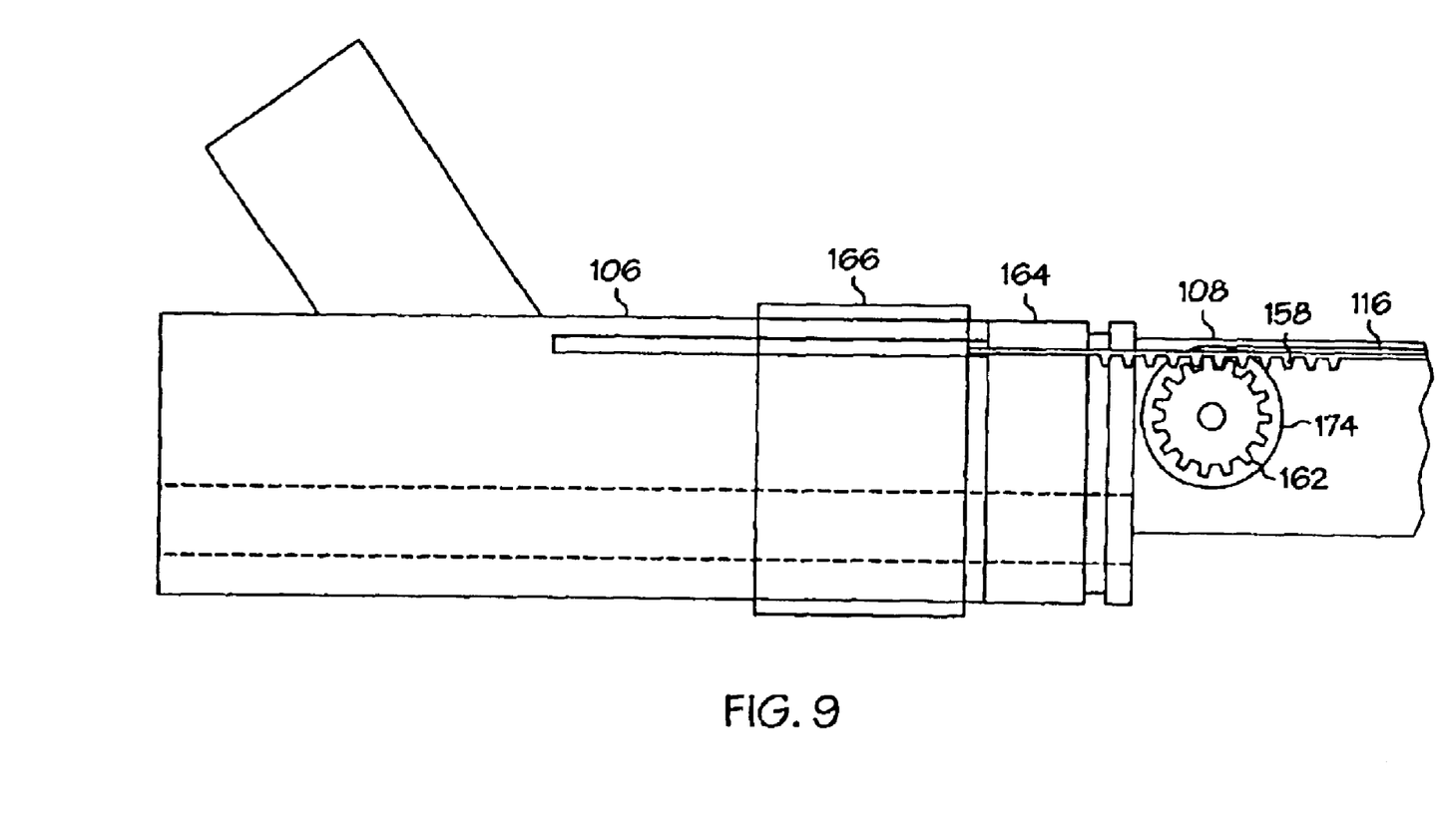
FIG. 9 shows a side view of a manifold according to the invention including a cross-sectional view of the distal end of the manifold.
Figure 10:
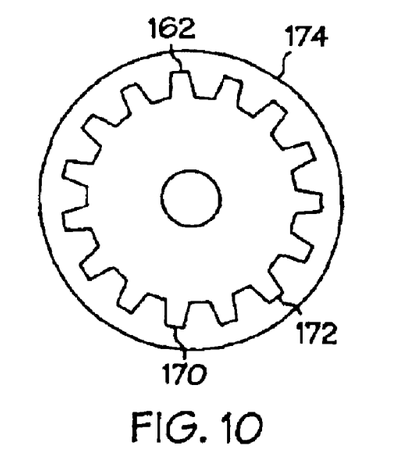
FIG. 10 shows a gear for use with a pinion.
Figure 11:
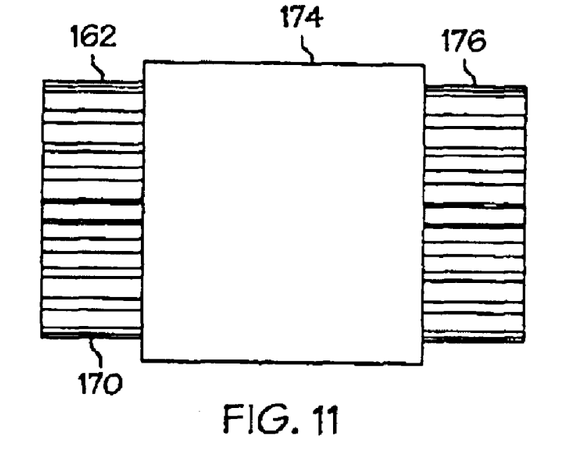
FIG. 11 shows a side view of a pinion.
Figure 12:
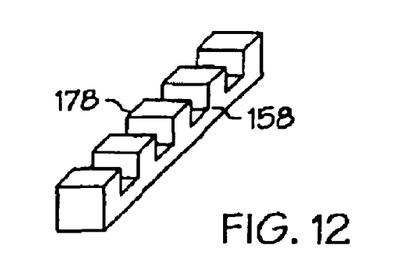
FIG. 12 shows a rack.

In another embodiment, as shown in FIGS. 1 and 9, the invention is directed to a medical device delivery system shown generally at 100 comprising a manifold 106 with an inner tube 108 extending proximally therefrom. A retractable sheath 114 is disposed about the distal end of inner tube 108. A pull wire 116 extends proximally from retractable sheath 114 to manifold 106. Manifold 106 includes a rack 158 and pinion 162. Rack 158 is movable in a proximal direction. Pinion 162, shown in greater detail in FIGS. 10 and 11, includes a gear portion 170 having a plurality of teeth 172 disposed about the periphery and a shaft portion 174 which serves as a spool for taking up the pull wire. Pinion 162 may optionally be provided with an enlarged end 176 to aid in retaining the pull wire on spool portion 174. Rack 158, as shown in FIG. 12, comprises a plurality of teeth 178 arranged linearly thereon. As rack 158 is moved in the proximal direction, rack 158 engages pinion 162 and pull wire 116 is wound around spool portion 174 of pinion 162 thereby retracting retractable sheath 114.

As the diameter of the spool portion of the pinion increases relative to the diameter of the gear portion, the mechanical advantage of the rack and pinion assembly increases reducing the length of rack necessary to retract the sheath by a fixed distance. While reducing the length of rack is desirable in that it allows for a reduced length manifold, if the mechanical advantage is excessive, the device will become more difficult to control as small, unintended displacements in the rack will result in large displacements of the retractable sheath. Moreover, as the mechanical advantage is increased, the force necessary to move the rack increases. Desirably, the ratio of the spool diameter to the gear diameter will range from 1:2 to 8:1 and more desirably, from 1:1 to 4:1.

Manifold 106 comprises a first part 164 and a second part 166. First part 164 is movably received in second part 166. Rack 158 is attached to second part 166 while pinion 162 is attached to first part 164. The invention also contemplates the use of manifolds with different designs. For example, the rack and pinion may be mounted within a one-piece construction manifold. In such an embodiment, the rack would be moved relative to the manifold itself to retract the retractable sheath.

Manifold 106 may, optionally, also slide in the distal direction. As the manifold slides in the distal direction, pull wire 116 unwinds from pinion 162. Desirably, a pull wire that is flexible enough to be wound and yet rigid enough to exert a pushing force to push the retractable sheath back into place as the pull wire unwinds will be used.

Figure 13:
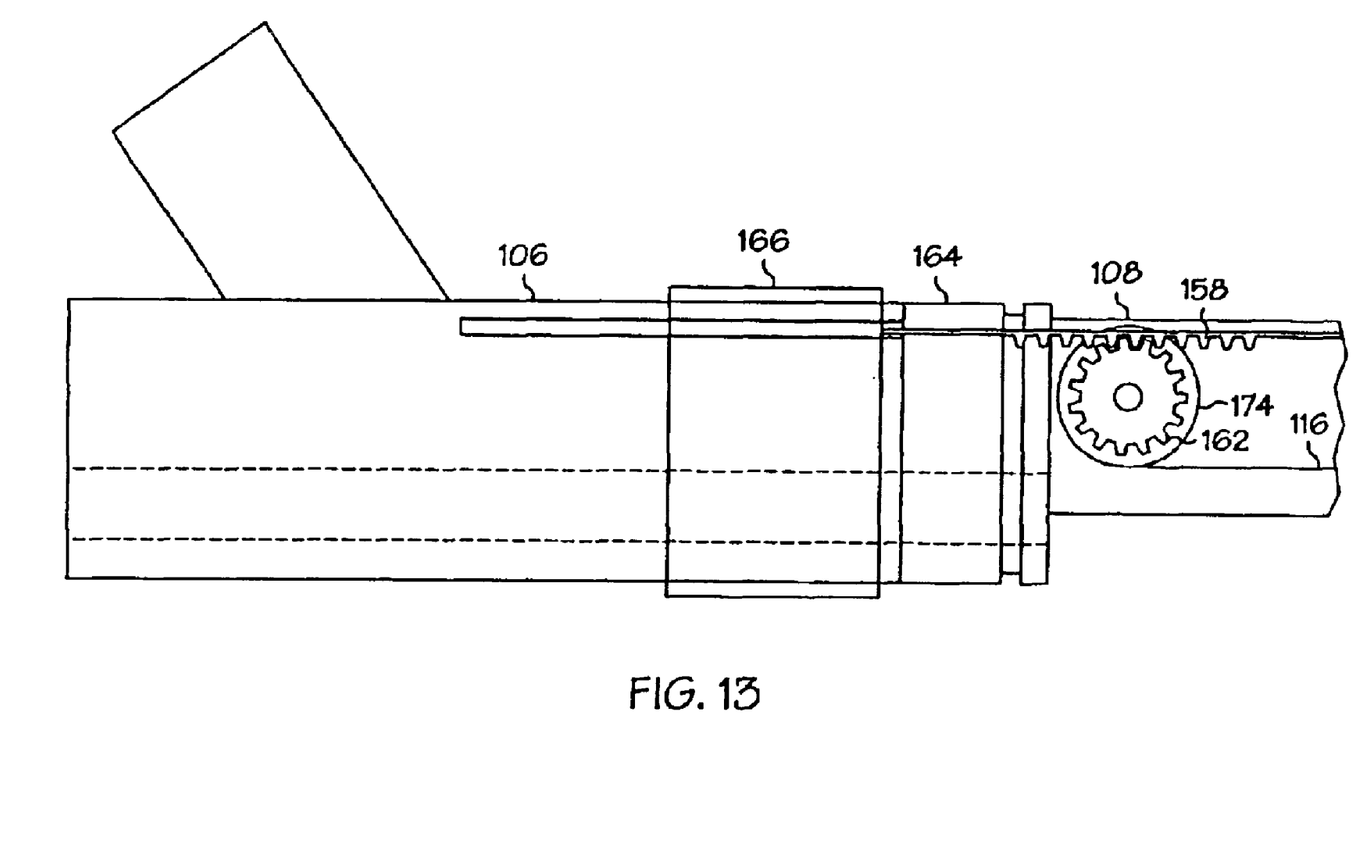
FIG. 13 shows a side view of a manifold according to the invention including a cross-sectional view of the distal end of the manifold.

As shown in FIG. 13, the medical device delivery system may also be arranged, by altering the direction that the spool is wound, so that retractable sheath 114 is retracted by sliding rack 158 in the distal direction.

Figure 14:
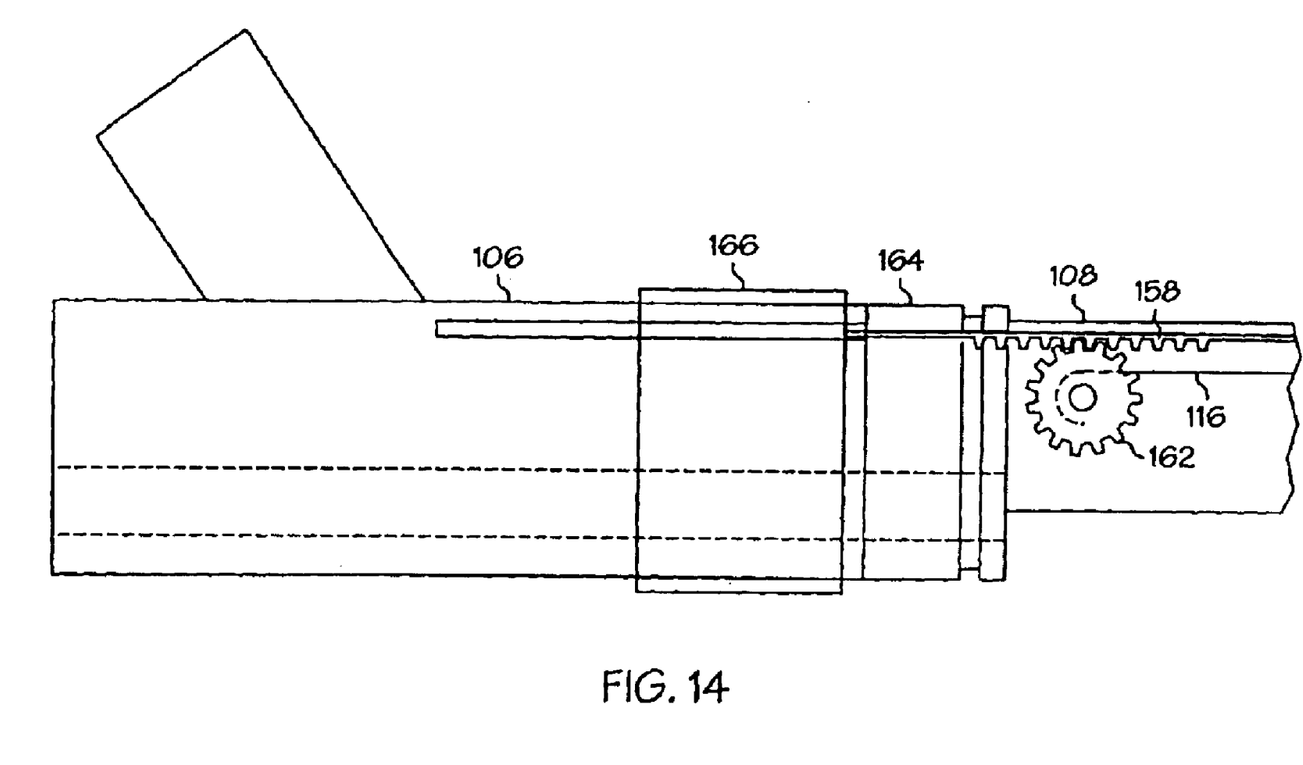
FIG. 14 shows a side view of a manifold according to the invention including a cross-sectional view of the distal end of the manifold.

The embodiments of FIGS. 9 and 13 employ a spool which has a radius larger than that of the pinion to achieve a force advantage. In another embodiment, as shown in FIG. 14, the invention is directed to a medical device delivery system which employs a spool 174 having a radius smaller than that of pinion 162 to achieve a distance advantage. Less force is required to retract the sheath, however, the rack must be moved a greater distance.

Figure 15:
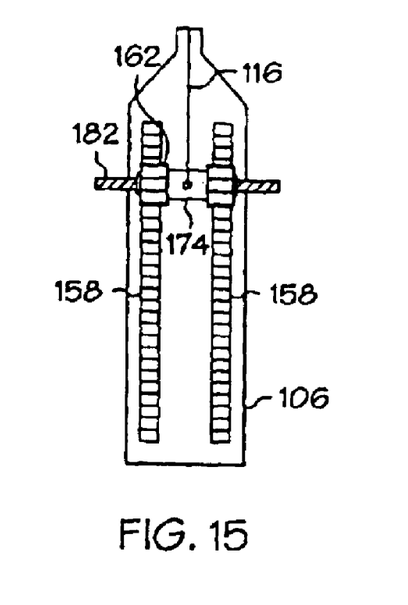
FIG. 15 shows a top view of a manifold according to the invention with parts cut away.
Figure 16:
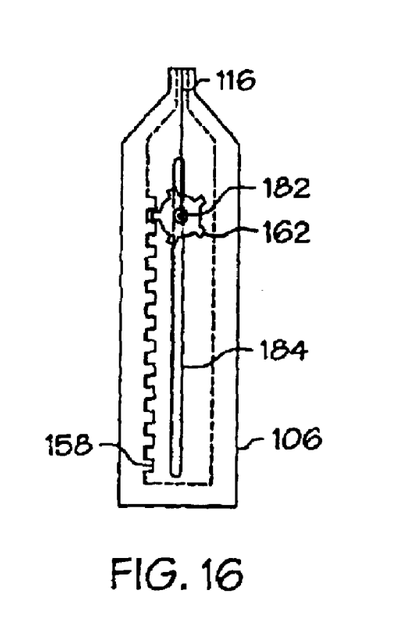
FIG. 16 shows a side view of the manifold of FIG. 15 with parts cut away.

In the above embodiments, the pinion is fixed in place and the rack is movable relative to the pinion. The invention also contemplates embodiments in which the rack is fixed in place and the pinion is movable relative to the rack. An example of such an embodiment is shown in FIGS. 15 and 16, FIG. 15 is a top view of a portion of a manifold 106 in which rack 158 is fixed in place and pinion 162 is movable relative to rack 158. FIG. 16 is a side view of manifold 106. Spindle 182 extends outward from pinion 162 through longitudinal slot 184 in manifold 106. Desirably, spindle 182 spins freely in pinion 162. As spindle 182 is moved in a proximal direction, pinion 162 moves in a proximal direction winding pull wire 116 around shaft portion 174 of pinion 162 thereby retracting in a proximal direction a retractable sheath (not shown) attached to the distal end of pull wire 116. The rack and pinion of FIGS. 15 and 16 may also be arranged such that retraction of the retractable sheath results from moving the spindle in a distal direction. The diameter of the shaft portion of the pinion may be altered relative to the diameter of the gear portion to increase or decrease the mechanical advantage of the device, as discussed above.

Where the inventive rack and pinion based medical device delivery system includes a bumper, the inventive shape memory bumper disclosed above may be used or any other suitable bumper may be used.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 1 or on claim 2; claim 5 may be taken as alternatively dependent from claims 2, 3 or 4; etc.).

What is claimed is:

1. A medical device delivery system comprising:
    a manifold having a rack and pinion, the rack slidable in a proximal direction;
    an inner tube having a proximal end and a distal end, the inner tube extending distally from the manifold;
    a retractable sheath disposed about the distal end of the inner tube; and
    a pull-wire extending proximally from the retractable sheath to the manifold, the pull wire attached to the pinion.

2. The medical device delivery system of claim 1 wherein the rack is movable in a distal direction.

3. The medical device delivery system of claim 1 wherein the retractable sheath is retracted by moving the rack in the proximal direction.

4. The medical device delivery system of claim 1 wherein the retractable sheath is retracted by moving the rack in the distal direction.

5. The medical device delivery system of claim 1 wherein the manifold comprises a first part and a second part, the first part movably received in the second part, the pinion disposed in the first part and the rack disposed in the second part.

6. The medical device delivery system of claim 1 further comprising a stent disposed about the inner tube and covered by the retractable sheath.

7. The medical device delivery system of claim 1 wherein the pinion comprises a gear portion and a spool portion for taking up the pull wire.

8. The medical device delivery system of claim 7 wherein the pull wire is wound around the spool portion when the rack is moved in a proximal direction.

9. The medical device delivery system of claim 1 wherein the pinion is movable in a proximal direction.

10. The medical device delivery system of claim 1 wherein the retractable sheath is retracted by moving the pinion in the proximal direction.

11. The medical device delivery system of claim 1, the pinion comprising a gear portion and a shaft portion in rotational cooperation with the gear portion, wherein the pull-wire is attached to the shaft portion.

12. The medical device delivery system of claim 11, wherein the shaft portion is spool-like and takes up the pull-wire when the gear portion rotates.

* * * * *